(12) United States Patent
Radeztsky

(10) Patent No.: US 6,708,059 B1
(45) Date of Patent: Mar. 16, 2004

(54) METHOD OF CORRECTING FOR PHASE ERROR INDUCED BY A DOWN SAMPLING ROUTINE

(75) Inventor: John H. Radeztsky, Milwaukee, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 0 days.

(21) Appl. No.: 09/233,683

(22) Filed: Jan. 19, 1999

Related U.S. Application Data
(60) Provisional application No. 60/072,248, filed on Jan. 23, 1998.

(51) Int. Cl.[7] ................................................ A61B 5/04
(52) U.S. Cl. ........................ 600/523; 600/485; 341/61
(58) Field of Search ............................ 327/91; 600/509, 600/523, 485; 341/61; 345/418

(56) References Cited

U.S. PATENT DOCUMENTS

| 4,819,252 A | * | 4/1989 | Christopher | 375/240 |
| 5,953,018 A | | 9/1999 | Lam | |
| 6,442,301 B1 | * | 8/2002 | Edgar | 382/275 |

* cited by examiner

Primary Examiner—Mark Bockelman
(74) Attorney, Agent, or Firm—Michael Best & Friedrich LLP

(57) ABSTRACT

A method and apparatus of correcting a data signal sampled at a first rate to a data signal displayed on a video monitor at a second rate is claimed. A data signal is received at a first rate. The data signal is separated into data windows. The minimum and maximum values and positions of data points in data windows are identified relative to a reference, and displayed on a video monitor.

16 Claims, 3 Drawing Sheets

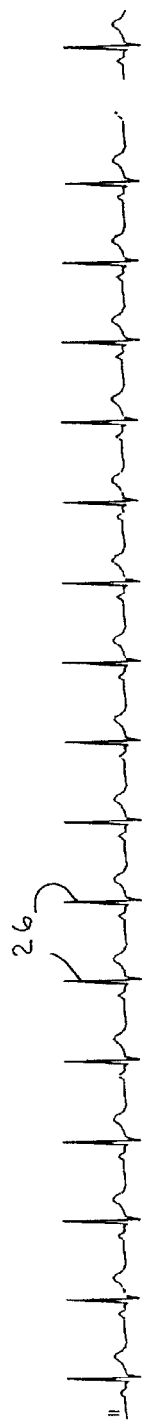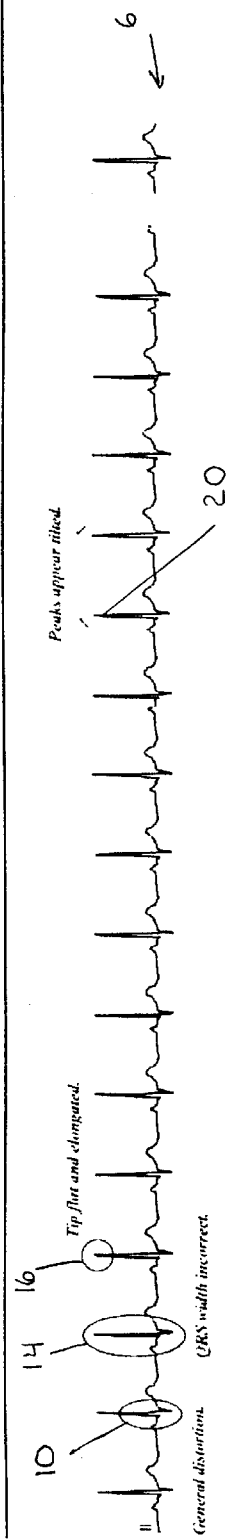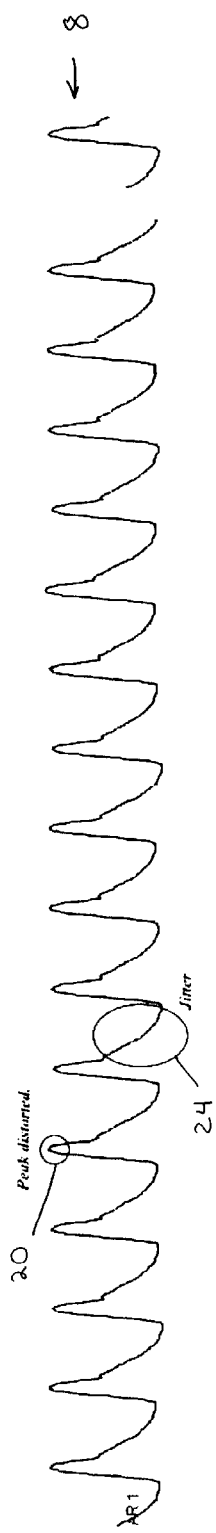
Phase Aligned
FIG. 1B
Without Phase Realignment
FIG. 1A

METHOD OF CORRECTING FOR PHASE ERROR INDUCED BY A DOWN SAMPLING ROUTINE

RELATED APPLICATIONS

This application claims the benefit under 37 C.F.R. §119 of prior filed, Provisional Application No. 60/072,248, filed on Jan. 23, 1998 now abandoned.

BACKGROUND OF THE INVENTION

The present invention generally relates to displaying of physiological data on patient monitors. More particularly, the present invention relates to a method and apparatus of correcting for phase error induced by down sampling of physiological data.

Patient physiological data, such as ECG data, is commonly displayed on patient monitors as a waveform suitable for review by medical care personnel. In order for medical care personnel to correctly assess the clinical import of the displayed information, it is highly desirable that the waveforms accurately reflect the measured physiological data regardless of the monitor type, pixel resolution, the size of the window in which the waveforms or other data are displayed or the speed at which the data is sampled. Generally, this has required some specific scale factor to be employed for each monitor type, pixel resolution capacity or display window size being employed.

SUMMARY OF THE INVENTION

One source of waveform distortion results from symmetrically plotting non-uniformly spaced selected data points in down-sampled data. When down-sampling data, features of the waveform in the original data may be lost or distorted by the down-sampling process. For example, the resolution of a standard cathode ray tube (CRT) monitor is not adequate for presenting full resolution ECG data. ECG data is typically received from the patient at a rate of about 480 Hertz $(Hz)_3$. The ECG data is filtered for electrical noise and other extraneous electrical information, reducing the data rate to about 240 Hz and presented to the clinician using a standard scroll rate of 25 millimeters (mm) per second (sec). A scroll rate of 25 mm/sec is a standard within the health care industry. A typical 21" CRT monitor displays a horizontal image size of approximately 406.4 mm with a horizontal screen resolution of 1280 pixels, or 3.15 pixels/mm. At a scroll rate of 25 mm/sec, each pixel represents approximately 12.7 milliseconds (ms) of data. Thus, if data is received at a 240 Hz rate, a data point is displayed on the CRT every 4.167 ms. This means that 3.05 data points will map to the same horizontal pixel location on the CRT. If the data is received at a different rate, e.g., 120 Hz (such as is the case with blood pressure waveforms) 1.52 data points will map to the same horizontal pixel location on the CRT. Plotting data as a waveform in this manner results in the plotting of different data points on the same pixel location. As a result, important physical features of the waveform representing the data may be lost.

Accordingly, the invention provides an interface for accurately displaying non-uniformly spaced selected data points in down-sampled data for a computer monitor display.

According to one aspect of the invention, a method and apparatus for synchronously plotting non-uniformly spaced selected data points in down-sampled data is provided. A data signal is received at a first rate and separated into at least one data window. Each data window has a predetermined number of data points having respective values. At least one of either a minimum and a maximum value of the data points are identified, thus identifying a position of the one of the minimum and maximum value relative to a reference. The data point is then displayed having the one of the minimum and maximum value at the position.

The invention also provides an apparatus having an input for receiving a data signal sampled at a first rate and means for converting the data signal to a second data signal sampled at a second lower rate and for displaying the second data signal on a video monitor.

It is an advantage of the invention to provide an interface for accurately displaying non-uniformly spaced selected data points in down-sampled data for a computer monitor display.

It is another advantage of the invention to provide a method and apparatus for synchronously plotting non-uniformly spaced selected data points in down-sampled data.

Other features and advantages of the invention will become apparent to those skilled in the art upon review of the following description, claims and drawings.

BRIEF DESCRIPTION OF THE DRAWINGS

FIG. 1A illustrates a prior art waveform wherein non-uniformly spaced data is plotted at fixed, regularly spaced intervals on the CRT.

FIG. 1B illustrates the same waveform produced by use of the present invention, plotting non-uniformly spaced data at varying intervals according to the invention.

Before one embodiment of the invention is explained in detail, it should be understood that the invention is not limited in its application to the details of the apparatus, composition or concentration of components, or to the steps or acts set forth in the following description. For example, the invention is capable of embodiments other than those adopted particularly for healthcare applications. Also, it should be understood that the phraseology and terminology used herein is for the purpose of description and should not be regarded as limiting.

DETAILED DESCRIPTION OF THE PREFERRED EMBODIMENT

Figure 2:
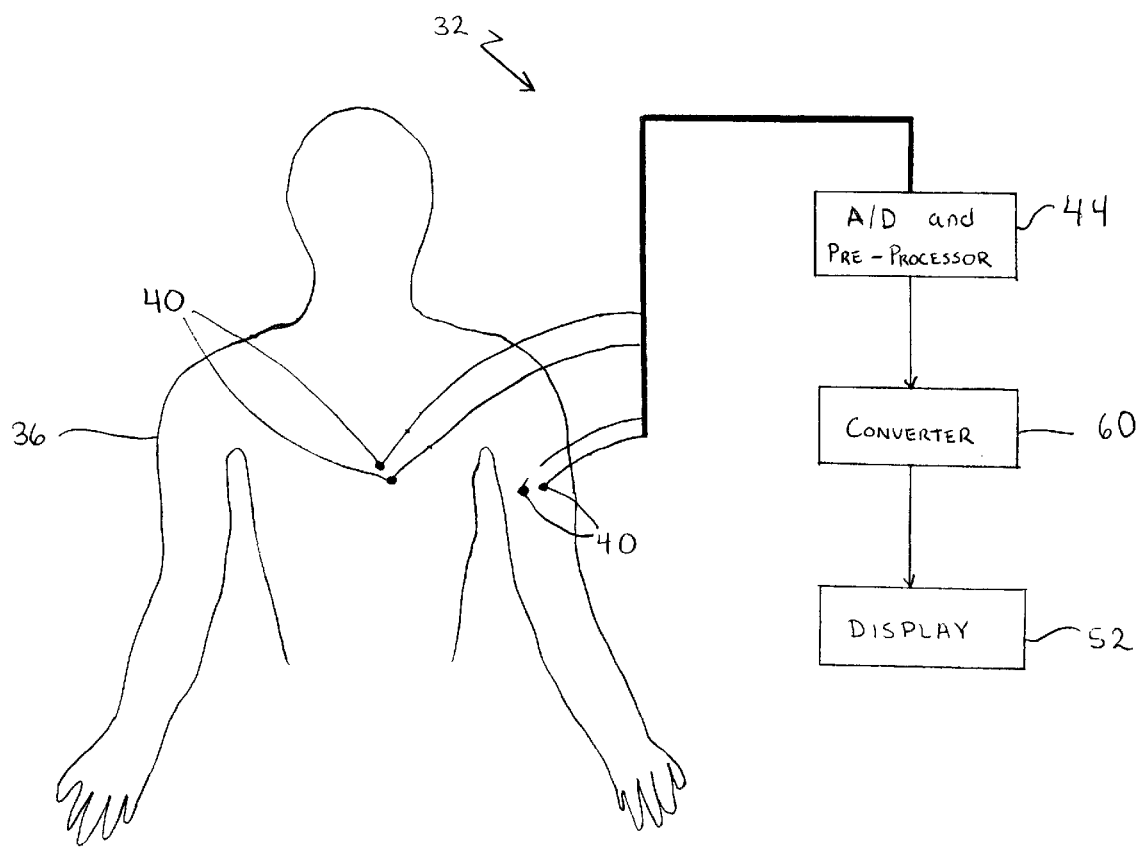
FIG. 2 is a block diagram illustrating a patient monitoring system according to the invention.

FIG. 2 illustrates the patient monitoring system 32 of the invention. The patient monitoring system 32 acquires and displays physiological patient data. While the monitoring system 32 can be used in connection with monitoring any kind of physiological parameter, in the preferred embodiment, the monitoring system 32 is for monitoring a patient's electrical cardiac activity and blood pressure. Monitoring system 32 is coupled to the patient 36 by an array of sensors or transducers which may include, for example, electrodes 40 mounted on the patient's chest and arm for electrocardiogram testing. Hereinafter, the term "sensor" and "transducer" will be used synonymously, and each term will be defined as including the subject matter of the other term.

The signals derived from the sensors are converted from analog form to digital form by an analog to digital converter (A/D) 44 and provided to a converter 60 that prepares the data for display on a display monitor 52. In the embodiment in FIG. 2, the A/D 44 further includes a pre-processor. The digital conversion by the A/D 44 is done at a rate of 480 Hz. The pre-processor then separates and filters the 480 Hz data into packets to be processed by the converter 60. Electrical noise and other extraneous electrical signals are filtered before the data is presented to the converter 60. The data rate after pre-processing is about 240 Hz. In other embodiments (not shown), if the signal collection rate is equal to or less than the rate at which the converter processes the data, the act of separating the data into packets by the pre-processor may be avoided.

The display monitor 52 is a conventional computer-style display monitor having a generally rectangular cathode ray tube (CRT). The CRT includes a plurality of pixels. The vertical location of the pixels is defined by a Y-coordinate and the horizontal location of the pixels is defined by an X-coordinate. As is known in the art, each pixel is capable of being energized electronically so that the pixel emits light visible to the user of the monitoring system.

Figure 3:
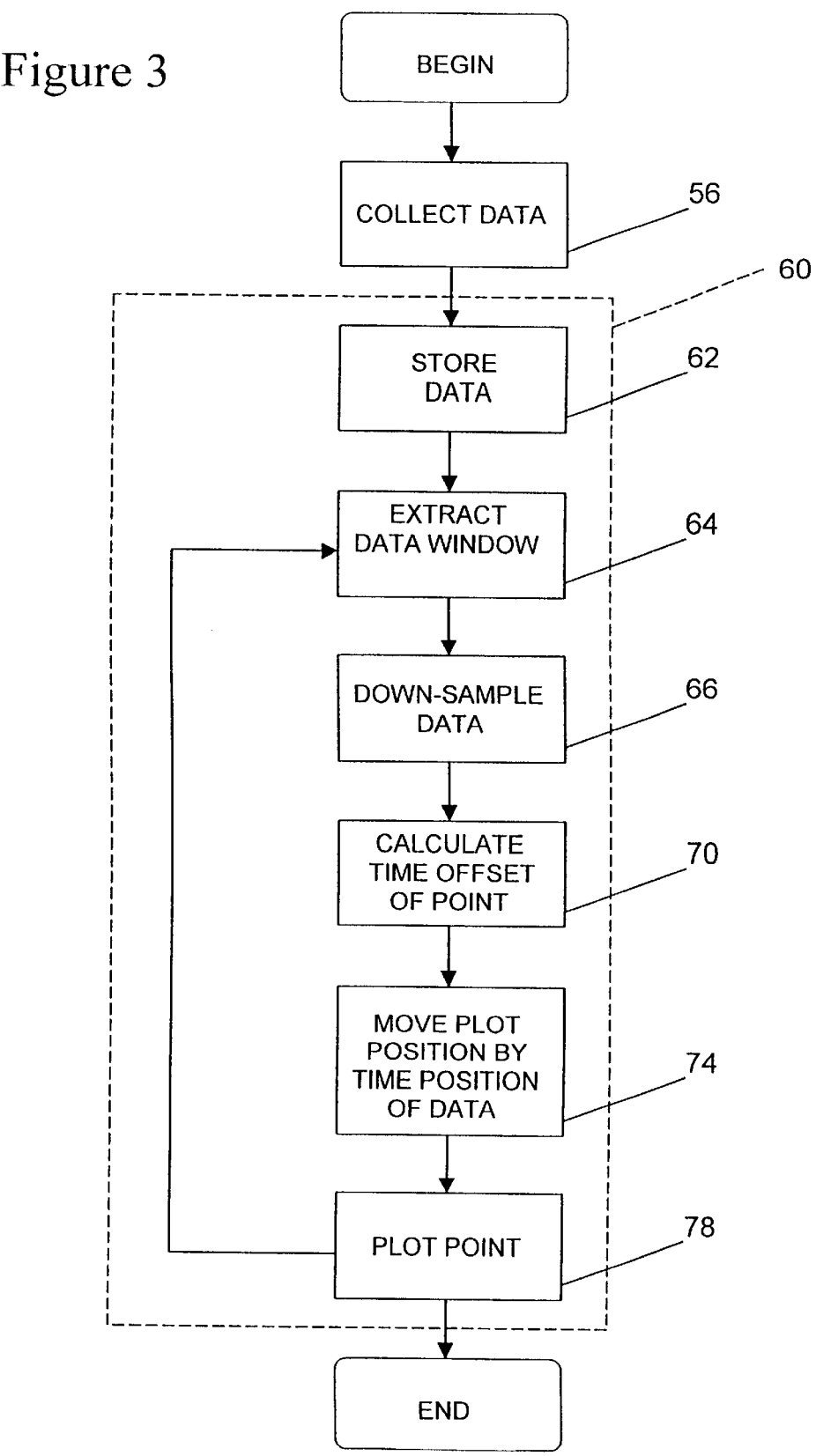
FIG. 3 is a flow chart illustrating the method of the invention.

FIG. 3 is a flowchart illustrating the operation of the patient monitoring system. The system collects physiological data (56) and pre-processes the data to a first rate, and converts the analog physiological data to digital data using an A/D converter. The converter (60) samples the collected, pre-processed physiological data 56 at a second rate, also called the update rate. The converter 60 may be resident in a stand alone bed-side computer system, or the converter 60 may be resident in a common network computer where physiological data from multiple patients may be centrally processed. The converter 60 generates a data signal having data points that are at approximately the same position as the data points had relative to one another in the originally sampled physiological data. In the converter 60, the data signal is typically temporarily stored (62) in a buffer until the data is processed. For ECG data, the data collection rate, or the sample rate, is about 240 Hz. For Blood Pressure (BP) data, the sample rate is about 120 Hz. The update rate operates at a predetermined speed. For all waveforms, including those composed of ECG and BP data, the update rate is about 60 Hz, although it is contemplated that other update rates may be used.

The collected physiological data is separated into portions or data windows, which are then extracted (64) from the buffer (62) to be processed. The number of data points comprising the data window is equal to the sample rate divided by the update rate. Thus, for ECG data, the data window is 240 Hz/60 Hz, or four data points. This is equal to about one point for every 16.667 ms of data.

In order to preserve the overall shape of the waveform, data points must be selected that best represent the waveform. Thus, the data window is down-sampled (66) by selecting, on the average, one data point from each data window. In one embodiment, the data point chosen is one of either a local minimum or a local maximum data point. In another embodiment, two data windows (comprising eight points) are considered together. This accommodates for situations in which it is desirable to choose more than one data point from within a single data window. If more than one data point is chosen within a single data window, no data points are chosen from the adjacent data window. Choosing more than one point in a single data window accommodates for situations in which more than one relative minimum or maximum data point occurs within a single data window, and no relative minimum or maximum data points occur in the adjacent data window. Thus, when two data windows are considered together, two of the eight data points comprising the two adjacent data windows are selected—the local minimum data point and the local maximum data point. In this manner, the overall shape of the waveform is best preserved.

In the original 240 Hz data stream, each data point is separated by a uniform 4.1667 ms, and each data window of four points is separated by a uniform 16.667 ms. However, as a result of down sampling, the resulting series of data points is not uniformly spaced. Thus, using the last data point of a data window as a reference, a time off-set for each data point is calculated (70). The time off-set is the time difference (or phase error) per point that is induced by fixed space plotting. The time off-set (in milliseconds) is calculated using the equation:

Time Off-Set$_{ms}$=[($R_s/R_u$)-$i$]*1000/$R_s$ where, $R_s$ is the sample rate (240 Hz),
$R_u$ is the update rate (60 Hz),
$i$ is the index number of the selected point, and
1000/$R_s$ is the time separation between points in ms (for ECG, 1000/240 HZ=4.167 ms).

The time off-sets for ECG data sampled at 240 Hz and operating at an update rate of 60 Hz are shown below:

| Data Point Selected | Time Off-Set |
| --- | --- |
| 4 | 0 ms |
| 3 | 4.167 ms |
| 2 | 8.333 ms |
| 1 | 12.5 ms |

A position to plot a data point is then determined (74), and plotted (78). The position to plot a data point is determined by moving from the current position by an amount equivalent to the time off-set for that data point. For example, if data point 4 is chosen from the first data window, and data point 3 is chosen from the second data window, the plot position for data point 3 is determined by moving forward the time off-set of four data points (16.667 ms), and then moving back by the time off-set of one data point (i.e., from the time of Data Point 4 to the time of Data Point 3), or 4.167 ms. Thus, data point 3 of the second data window is plotted 16.667 ms–4.167 ms, or 12.5 ms from data point 4 of the first data window. Moving forward by 16.667 ms is based on the update rate of 60 Hz. Moving forward at a constant 16.667 ms allows the multiple waveforms to be updated synchronously.

After a data point is plotted, the next data window of physiological data is extracted (64) from the buffer (62). The process is repeated until all of the data is processed.

Multiple waveforms may also be displayed in any given window. Because real time data is being displayed, a constant, periodic update is preferred. If the update to the display is not constant, a noticeable jerkiness may be apparent to the human eye. In addition, each of the waveforms on the display will potentially have different points selected within the data window. The update rate, however, is constant for all waveforms plotted. Thus, the presentation for all of the waveforms on the display is moved forward at a fixed rate, and the display is updated with all data that has occurred since the previous update.

FIG. 1A illustrates an ECG waveform 6 and a blood pressure waveform 8 wherein non-uniformly spaced 60 Hz data is plotted at fixed, regularly spaced intervals on the CRT as is done in the prior art. Plotting in such a fashion (in effect) shifts the data points relative to one another resulting in distortion of the waveform's shape.

As shown in FIG. 1A, general distortion due to small, rapid variations in the size, shape or position of observable information may occur, as indicated by the region of the waveform indicated by reference numeral 10. Distortion of the QRS width may occur, as illustrated by reference numeral 14. Aberrations of the size or position of tips of waveforms may also occur, as indicated by the elongated and flat tips shown by reference numeral 16. Waveform peaks may also appear tilted or distorted, as indicated by reference numeral 20. Further, time, amplitude, frequency or phase related jitter may be present, as indicated by the change in slope of the waveform shown by reference numeral 24.

FIG. 1B illustrates a waveform produced using the down sampling technique of the present invention. In FIG. 1B, non-uniform data points are plotted as they occur, i.e., at uneven spacing as calculated by converter 60. As shown, the ECG data as plotted according to the invention contains sharp QRS spikes 26 that play an important roll in the assessment of a patient's condition.

Thus, the plotting of physiological data using the present invention minimizes distortions and aberrations caused by down-sampling the rapid variations inherent in physiological data, and is more reflective of the true waveform, providing a more accurate depiction of features such as QRS width, tips and peaks present of the waveform, and slope variations of the waveform.

Various features of the invention are set forth in the following claims.

What is claimed is:

1. An apparatus comprising:

an input for receiving a first data signal sampled at a first rate; and means for converting the first data signal to a second data signal sampled at a second rate and for calculating a phase error for each data point included in the second data signal and for displaying each data point of the second data signal on a video monitor based on the corresponding calculated phase error.

2. The apparatus of claim 1, wherein multiple first data signals are received at approximately the same time.

3. The apparatus of claim 1, further comprising a separator to separate the first data signal into at least one data window.

4. The apparatus of claim 3, wherein the data window has a predetermined number of data points having respective values.

5. The apparatus of claim 3, wherein the separator separates the data signal into groups of two data windows.

6. The apparatus of claim 5, wherein the separator selects the position of a minimum data point value and the position of a maximum data point value.

7. The apparatus of claim 1, wherein the first rate is approximately 240 Hertz.

8. The apparatus of claim 1, wherein the first rate is approximately 120 Hertz.

9. The apparatus of claim 1, wherein the second rate is less than the first data rate.

10. The apparatus of claim 1, wherein the second rate is approximately 60 Hertz.

11. An apparatus comprising:

an input for receiving a first data signal sampled at a first rate;

a converter for sampling the first data signal at a second rate to generate therefrom a second data signal having a first data point and a second data point and for calculating a first time off-set from a reference point for the first data point and for calculating a second time off-set from a reference point for the second data point; and a display for displaying the first data point of the second data signal and the second data point of the second data signal, the first data point and the second data point being displayed on the display according to the first time off-set and the second time off-set, respectively.

12. The apparatus as set forth in claim 11, wherein the time off-set for the first data point is the phase error for the first data point that is induced by fixed space plotting, and the time off-set for the second data point is the phase error for the second data point that is induced by fixed space plotting.

13. The apparatus as set forth in claim 11, wherein the display is a video monitor.

14. The apparatus as set forth in claim 11, wherein the first data signal is an electrocardiogram data signal.

15. The apparatus as set forth in claim 11, wherein the first data signal is a blood pressure data signal.

16. The apparatus as set forth in claim 11, wherein the apparatus is a patient monitoring system.

* * * * *